(12) United States Patent
Daage et al.

(10) Patent No.: US 6,800,579 B2
(45) Date of Patent: Oct. 5, 2004

(54) CATALYST REGENERATION

(75) Inventors: Michel Daage, Baton Rouge, LA (US); Russell John Koveal, Baton Rouge, LA (US); Min Chang, McLean, VA (US)

(73) Assignee: ExxonMobil Research and Engineering Company, Annandale, NJ (US)

(*) Notice: Subject to any disclaimer, the term of this patent is extended or adjusted under 35 U.S.C. 154(b) by 207 days.

(21) Appl. No.: 10/059,926

(22) Filed: Jan. 29, 2002

(65) Prior Publication Data

US 2003/0144366 A1 Jul. 31, 2003

(51) Int. Cl.[7] .......................... B01J 38/12; B01J 38/10; B01J 38/06; C07C 27/00
(52) U.S. Cl. ............................ 502/38; 502/53; 502/55; 518/700; 518/709; 518/710; 518/713; 518/714; 518/715; 518/716
(58) Field of Search ........................... 502/38, 53, 55; 518/700, 709, 710, 713–716

(56) References Cited

U.S. PATENT DOCUMENTS

| | | | |
|---|---|---|---|
| 2,348,418 A | 5/1944 | Roesch et al. | 196/52 |
| 2,369,956 A | 2/1945 | Feisst et al. | 260/449.6 |
| 2,481,841 A | 9/1949 | Hemminger | 252/454 |
| 2,542,558 A | 2/1951 | Naragon et al. | 252/416 |
| 2,582,713 A | 1/1952 | Martin et al. | 252/418 |
| 3,256,205 A | 6/1966 | Constabaris et al. | 252/413 |
| 3,661,798 A | 5/1972 | Cosyns et al. | 252/416 |
| 3,839,191 A | 10/1974 | Johnson | 208/108 |
| 4,191,664 A | 3/1980 | McArthur | 252/466 |
| 4,399,234 A | 8/1983 | Beuther et al. | 518/715 |
| 4,795,726 A | 1/1989 | Schaper et al. | 502/26 |
| 4,814,066 A | 3/1989 | Fu | 208/120 |
| 4,888,131 A | 12/1989 | Goetsch et al. | 252/373 |
| 4,929,336 A | 5/1990 | Lowery et al. | 208/120 |
| 4,954,244 A | 9/1990 | Fu et al. | 208/120 |
| 4,978,689 A | 12/1990 | Bell et al. | 518/709 |
| 5,071,538 A | 12/1991 | Clark et al. | 208/112 |
| 5,154,819 A | 10/1992 | Clark et al. | 208/216 R |
| 5,160,456 A | 11/1992 | Lahn et al. | 252/373 |
| 5,283,216 A | 2/1994 | Mitchell | 502/30 |
| 5,292,705 A | 3/1994 | Mitchell | 502/325 |
| 5,389,592 A | 2/1995 | Weissman et al. | 502/25 |
| 5,438,028 A | 8/1995 | Weissman et al. | 502/202 |
| 5,495,055 A | 2/1996 | Rueter | 568/881 |
| 5,728,918 A | 3/1998 | Nay et al. | 585/733 |
| 5,928,980 A | 7/1999 | Gangwal et al. | 502/20 |
| 5,977,192 A | 11/1999 | Howsmon et al. | 518/700 |
| 6,121,333 A * | 9/2000 | Clerici et al. | 518/715 |
| 6,201,030 B1 | 3/2001 | Beer | 518/709 |
| 6,331,574 B1 * | 12/2001 | Lapidus et al. | 518/709 |

FOREIGN PATENT DOCUMENTS

| | | | | |
|---|---|---|---|---|
| DE | 119138 | | 4/1976 | B01J/11/18 |
| DE | 4302992 A1 | | 8/1994 | B01J/23/94 |
| EP | 0244014 B1 | | 11/1987 | B01J/38/64 |
| EP | 0244014 A2 | | 11/1987 | B01J/38/64 |
| EP | 0583837 A1 | | 2/1994 | B01J/37/00 |
| EP | 0583837 B1 | | 2/1994 | B01J/37/00 |
| EP | 0979673 A1 | | 2/2000 | B01J/37/02 |
| GB | 533459 | | 2/1941 | |
| WO | WO 98/27181 | | 6/1998 | C01G/2/00 |

OTHER PUBLICATIONS

A. Khodakov et al., "Structural Modification of Cobalt Catalysts: Effect of Wetting Studied by X–Ray and Infrared Techniques", *Oil & Gas Science and Tehcnology*, Rev. IFP, vol. 54 (1999), No. 4. pp.525–535.

* cited by examiner

Primary Examiner—Stanley S. Silverman
Assistant Examiner—Jonas N. Strickland
(74) Attorney, Agent, or Firm—Mark D. Martin

(57) ABSTRACT

There is provided a process for regenerating the activity of used metal catalysts for the hydrogenation of carbon monoxide comprising decreasing the hydrocarbon content thereof, calcining under an oxidant-containing atmosphere, impregnating with a solution of at least one of a metal compound, calcining under an oxidant-containing atmosphere and activating by contacting with a hydrogen-contacting gas at elevated temperatures to form an active catalyst. The process regenerates and enhances both supported and dispersed active metal (DAM) catalysts. Used catalysts enhanced by the process are initially treated to decrease their hydrocarbon content. The treatment may be carried out in a single reactor, or by carrying out up to all steps after catalyst may be withdrawn from a reactor and returned to at least one reactor, both preferably during operation thereof. Up to all steps may be effected in a subsequent reactor, or in specialized apparatus.

33 Claims, No Drawings

CATALYST REGENERATION

RELATED APPLICATIONS

The assignee of this application is filing herewith the following applications: Ser. No. 10/059,916, entitled "Fischer-Tropsch Catalyst Enhancement"; Ser. No. 10/059,917, entitled "Supported Catalyst Regeneration"; Ser. No. 10/059,918, entitled "Supported Catalyst Activation; Ser. No. 10/059,928, entitled "Supported Catalyst Treatment"; and Ser. No. 10/059,927, entitled "Catalyst Enhancement". Also related in pending application Ser. No. 09/628,047, filed Aug. 1, 2000, entitled "process for Increasing Cobalt Catalyst Hydrogenation Activity Via Aqueous Low Temperature Oxidation".

This invention relates to the production of higher hydrocarbons from synthesis gas utilizing a metal catalyst, particularly a cobalt catalyst.

BACKGROUND OF THE INVENTION

The conversion of synthesis gas, i.e. carbon monoxide and hydrogen, to higher value products is well known and has been in commercial use for many years. Typical processes include, for example, methanol syntheses, higher alcohol synthesis, hydroformylation and Fischer-Tropsch synthesis. The synthesis gas mixture is contacted with a suitable catalyst typically comprising at least one Group VIII metals. Suitable Fischer-Tropsch catalysts comprise one or more catalytic Group VIII metals, such as iron, cobalt and nickel. For oxygenate synthesis, copper may be included as well.

There exist many variations of the formulation and preparation of catalysts useful for the conversion of synthesis gas. In general, the catalysts are classified into two broad types, unsupported metals, known as Dispersed Active Metals and a larger groups of catalysts metals supported on refractory oxides, such as silica, alumina, titania or mixtures thereof. Such catalysts, whether supported or unsupported may be enhanced by the addition of other metals or metal oxides, known as promoter metals.

Supports for catalyst metals are generally pilled, pelleted, beaded, extruded, spray-dried or sieved materials. There are many methodologies reported in the literature for the preparation of supported catalyst metals. Examples of such techniques include incipient wetness impregnation, slurry impregnation, coprecipitation, and the like. It will be appreciated that high metal loadings are generally obtained by coprecipitation or multiple, i.e. two or three, impregnations, whereas low metal loading catalysts may be prepared utilizing a single impregnation. The catalyst metal content of such catalysts may vary from one to fifty weight percent. Promoter metals or metal oxides may be added during the impregnation steps using soluble salts of the respective metals such as Pt, Pd, Rh, Ru, Os, Ir, Mo, W, Cu, Si, Cr, Ti, Mg, Mn, Zr, Hf, Al, Th and the like. It will further be appreciated that the choice of a particular metal combination and the amount thereof to be utilized will depend upon the specific application used in the conversion of synthesis gas. When a suitable support has been impregnated with one or more metals as by impregnation to form a catalyst precursor, it may be dried and then calcined in an oxygen-containing environment. The precursor is thereafter activated by reduction at elevated temperature in the presence of a reducing gas, typically containing hydrogen. Optionally, the catalyst is activated by contacting with hydrogen gas in presence of liquid hydrocarbons as disclosed in U.S. Pat. No. 5,292,705.

Regardless of the particular formulation and method of preparation, all catalysts lose productivity and/or selectivity in use. Selectivity may vary with the particular synthesis, but is generally expressed in terms of the percent of an undesirable substance in the product mix. For example, methane selectivity in a Fischer-Tropsch reaction is the percent of methane formed with the desired higher hydrocarbons. Degradation of the catalyst productivity may be due to a number of phenomena including, without limitation, contamination by catalytic poisons, deposition of carbonaceous residues, sintering, phase transformation of the metal or metals and the like. U.S. Pat. No. 5,283,216 discloses a method for rejuvenating a hydrocarbon synthesis catalyst, which has been subjected to reversible, partial deactivation in a slurry synthesis process by contacting the catalyst with hydrogen at elevated temperatures in presence of liquid hydrocarbons. However, not all deactivated catalysts are rejuvenable. It is commercially significant to extend the useful life of a used catalyst by various treatment procedures, for example, by means of regeneration.

There are catalyst regeneration methods described in the literature. Typically, these techniques rely on contacting the used catalyst at elevated temperature with an oxygen-containing gas and/or steam. Such treatment may be used to remove carbonaceous deposits and poisons additionally converting the metal to its corresponding oxide or oxides. The regenerated catalyst is thereafter reactivated by means of a reduction with a hydrogen-containing gas at elevated temperatures. Such a treatment is described, for example, in U.S. Pat. No. 4,399,234.

There are catalyst regeneration methods described in the literature. Typically, these techniques rely on contacting the used catalyst at elevated temperature with an oxygen-containing gas and/or steam. Such treatment may be used to remove carbonaceous deposits and poisons additionally converting the metal to its corresponding oxide or oxides. The regenerated catalyst is thereafter reactivated by means of a reduction with a hydrogen-containing gas at elevated temperatures. Such a treatment is described, for example, in U.S. Pat. No. 4,399,234.

U.S. Pat. No. 2,369,956 discloses a method for regeneration of a Fischer-Tropsch catalyst wherein the catalyst is dissolved and subsequently restored by re-precipitation of the catalytic metals. It was noted, however, that there were deposits remaining in the contact substance that materially increased the difficulty of restoring the catalyst. An example of such substances is the high molecular weight paraffins from the used catalyst that make it difficult to filter the metal salt produced by dissolution of the catalyst with acid. Since these materials make purification of the salt difficult, it is taught in the patent that hydrocarbon deposits on the catalyst must be initially removed by treatment with flowing hydrogen at elevated temperatures. The process of dissolution and re-precipitation may then be carried out. It is also taught in the patent that the pyrophoricity of the treated catalyst might be mitigated by treatment with steam prior to dissolution with strong acid. However, there is nothing in the patent regarding the efficiency of the disclosed process or the effect of exposing a catalyst support, such as described above, with strong acid.

U.S. Pat. No. 3,256,205 discloses a method of catalyst regeneration by treatment with a strong acid to the point of incipient wetness of the catalyst prior to removal of carbonaceous deposits accumulated during the catalytic cycle. It is specifically stated that removal of the carbonaceous deposits is detrimental in that the catalyst support would be damaged by contact with the strong acid utilized. Suitable acids are stated as having a dissociation constant greater that $10^{-2}$ and are added to the catalyst in an amount varying from 0.5 stoichiometry to the stochiometry required to form the salts of the metals present in the catalyst.

It is clear from the foregoing discussion that there is not a clear incentive in the art to utilize any particular methodology in attempting to improve on the process of catalyst regeneration. In fact, the two patents discussed above would appear to negate each other since the first teaches that it is necessary to remove the carbonaceous deposits from the catalyst prior to treatment with acid, yet the second teaches that the carbonaceous deposits are necessary to prevent the acid from attacking the support structure. It also must be considered that it is generally not possible to use an aqueous-based solvent on a catalyst containing a waxy hydrocarbon deposit because it is hydrophobic as typically observed with Fischer-Tropsch catalysts. Hence, it would appear that the process of the second patent would not have applicability to a Fischer-Tropsch catalyst since a characteristic of the process is that the pores of the used catalyst are filled with wax that prevents good wetting by aqueous treatment solutions.

In hydroprocessing and oxidation catalysts, carbonaceous deposits are typically removed by calcination with an oxygen-containing gas at elevated temperatures. During such treatments, the metal-containing active phase of the catalyst is converted to oxides. To further improve the recovery of catalytic activity, contaminating metals are then removed by treatment with a basic solution, particularly one containing ammonium carbonate or sodium cyanide. Such treatments are illustrated, for example, in U.S. Pat. No. 4,795,726 and German Patent DE 43 02 992.

The modifying of hydroprocessing catalysts is taught, for example, in U.S. Pat. No. 5,438,028 wherein a finished catalyst is enhanced by the addition of a modifying agent in solution after which the catalyst is dried and optionally heated to a temperature of from 120° C. to about 1000° C. The process does not include a final reduction step to reactivate the catalyst. The modifiers disclosed in column three, with the exception of boron, which is not a metallic element, are all recognized poisons for Fischer-Tropsch catalysts. U.S. Pat. No. 5,389,502 discloses application of the same process for the enhancing of a hydroprocessing catalyst that has been regenerated by an oxidative treatment. The application of the modifying agent to the surface of the catalyst may be carried out to the point of incipient wetness. In both of these patents, the preferred modifying agent is boron.

U.S. Pat. No. 6,201,030 discloses a process and apparatus for regenerating a particulate catalyst during operation of a reactor. The process consists of withdrawing a partially spent catalyst as a slurry from a reactor to one of two regeneration stations, operating in parallel, treating the slurry with hydrogen and returning it to the reactor. The two regenerating stations are utilized in the alternative operating out of phase thereby facilitating continuous withdrawal and return of the slurry without substantial change in the liquid level within the reactor. The disclosed process effectively fails to provide any means of regenerating severely deactivated catalyst or of improving process reliability, such as by removing fines that may have formed in the turbulent environment of the reactor.

It is generally recognized that the economic worth of a given catalyst is a function of its original cost, its activity its regenerability and its value as a used catalyst, e.g. for metals recovery. It is apparent from the foregoing discussion that there has been considerable effort going back over many years to improve the economic worth of catalysts, since a process that will effectively increase the value of a catalyst and/or extend the useful life thereof before it must be disposed of through conventional metal recovery will significantly improve the worth of that catalyst. Effective catalyst regeneration effected while at the same time maintaining the reliability of the process requires the use of specific apparatus or combinations of specialized pieces of apparatus in combination with specific treatment techniques. Such process techniques and apparatus for carrying them out are provided in accordance with the present invention.

SUMMARY OF THE INVENTION

In accordance with the present invention, there is provided a significant improvement in the catalytic hydrogenation of carbon monoxide to form a mixture of hydrocarbons wherein the catalyst is a Fischer-Tropsch metal catalyst. The useful life of used Fischer-Tropsch catalysts is extended by a process of regeneration comprising: initially decreasing the hydrocarbon content thereof, calcining in the presence of an oxidant-containing atmosphere; impregnating with a solution of a compound at least one of a catalyst metal and a promoter metal for the catalyst; calcining again in the presence of an oxidant-containing atmosphere and finally reducing by treatment with a hydrogen-containing gas at elevated temperatures to form an active catalyst. Preferably, the catalyst particles are dried preceding each calcining step. The catalyst may also be passivated after the activation step.

The catalyst treated according to the invention is advantageously reused for the hydrogenation of carbon monoxide. Optionally, the catalyst is withdrawn from a carbon monoxide hydrogenation reactor and returned to at least one reactor, preferably during operation of the reactors. One up to all of the treating steps through activation of the catalyst may be carried out prior to withdraw, subsequent to return, or between withdraw and return. The withdraw and return steps may be carried out periodically or continuously.

DETAILED DESCRIPTION OF THE INVENTION

The catalyst metal substrates treated in accordance with the process of the present invention are selected from the group consisting of Co, Ni, Cu, Ru, Rh, Pd, Os, Ir, Re and Pt with cobalt and ruthenium being preferred. The process of the present invention is applicable to both supported and unsupported catalysts. Unsupported catalysts be in a variety of forms such as gauzes, fibers, wools and the like, but are preferably particulates since particulates have more surface available for enhancement of catalytic activity by the subject process Preferred unsupported catalyst substrates are Dispersed Active Metals ("DAM") which are primarily, i.e. at least about 50 wt. %, preferably at least 80 wt. %, composed of one or a mixture of metals such as described above and are, without further treatment, capable of catalyzing Fischer-Tropsch synthesis. DAM catalysts may be prepared by any of a number of art-recognized processes. The particle size range for the metal substrate particulates of the process is generally from about 0.1 micron to 5 millimeters, preferably from about 1 to 50 microns at their significant dimension. The term "significant dimension" as utilized herein will vary depending on the form of the substrate metal. Wherein the metal is a wire or a spheroid, the significant dimension is the diameter thereof, for an oval or a rhomboid or an irregular shape, the significant dimension is the smallest thickness.

Supported metal catalysts, which correspond essentially to reduced metals formed by one of the recognized techniques discussed above onto a suitable support structure, typically a refractory inorganic oxide, such as titania, silica, silica-alumina, aluminum and the like, are utilized in a broad range of applications such as hydrogenation of hydrocarbons and carbon monoxide. Titania is a preferred support material for the catalyst metal substrates treated in accordance with the present invention. Start-up procedures for such reactions, which may include specific activation sequences, are highly dependent upon the catalytic reaction, the process design and, in particular, the reaction vessel design and configuration. The slurry bubble column reactor, is a preferred vessel for carrying out carbon monoxide hydrogenation. The use of slurry bubble column for CO hydrogenation is particularly convenient in combination with the catalyst regeneration process of the present invention. In such reactors, the solid phase catalyst is dispersed or held in suspension in a liquid hydrocarbon phase by a gas phase, which continuously bubbles through the liquid phase. Supported catalysts useful for such applications contain at least 5 wt. %, preferably from 10 to 50 wt. %, of the catalyst metal in the reduced metallic form.

In the carbon monoxide hydrogenation reaction, syngas comprising a mixture of hydrogen and carbon monoxide is contacted with the catalyst thereby being converted into liquid and gaseous products, preferably $C_{10+}$ liquid hydrocarbons, with shifting or non-shifting conditions, preferably the latter, wherein little or no water gas shift takes place. This hydrocarbon synthesis ("HCS") process is generally carried out at temperatures of from about 160° C. to 260° C., pressures of from about 1 atm to about 100 atm, preferably from 10 atm to 40 atm, and gas space velocities of from about 100 V/Hr/V to about 40,000 V/Hr/V, preferably from about 1,000 V/Hr/V to about 15,000 V/Hr/V. The expression "V/Hr/V" represents the standard volumes of gaseous carbon monoxide and hydrogen mixtures at 25° C. and 1 atm per hour per volume of catalyst, respectively. The molar ratio of hydrogen to carbon monoxide in the syngas feed is about 2.1:1 for the production of higher hydrocarbons. This ratio may vary to from about 1:1 to 4:1, and preferably is from about 1.8:1 to 2.2:1. These reaction conditions are well known and a particular set of reaction conditions can readily be determined from the parameters given herein. The hydrocarbon-containing products formed in the process are essentially free of sulfur and nitrogen-containing contaminants.

The hydrocarbons produced in a process as described above are typically upgraded to more valuable products by subjecting all or a portion of the $C_{5+}$ hydrocarbons to fractionation and/or conversion. By "conversion" is meant one or more operations in which the molecular structure of at least a portion of the hydrocarbons is changed and includes both non-catalytic processing, e.g. steam cracking, and catalytic processing, e.g. catalytic cracking, in which the portion, or fraction, is contacted with a suitable catalyst. If hydrogen is present as a reactant, such process steps are typically referred to as hydroconversion and variously as hydroisomerization, hydrocracking, hydrodewaxing, hydrorefining and the like. More rigorous hydrorefining is typically referred to as hydrotreating. These reactions are conducted under conditions well documented in the literature for the hydroconversion of hydrocarbon feeds, including hydrocarbon feeds rich in paraffins. Illustrative, but non-limiting, examples of more valuable products from such feeds by these processes include synthetic crude oil, liquid fuel, emulsions, purified olefins, solvents, monomers or polymers, lubricant oils, medicinal oils, waxy hydrocarbons, various nitrogen- or oxygen-containing products and the like. Examples of liquid fuels includes gasoline, diesel fuel and jet fuel, while lubricating oil includes automotive oil, jet oil, turbine oil and the like. Industrial oils include well drilling fluids, agricultural oils, heat transfer oils and the like.

The syngas utilized in carbon monoxide hydrogenation may be formed by various means known to those of ordinary skill in the art, such as a fluid bed syngas generating unit as is disclosed, for example, in U.S. Pat. Nos. 4,888,131, and 5,160,456. Regardless of the source, syngas typically may contain chemical species, such as hydrogen cyanide, which over time cause deactivation of the catalyst. Other deactivating chemical species may be formed during the carbon monoxide hydrogenation process itself. It is generally recognized that deactivation by those contaminants can be reversed by treatment with hydrogen thereby renewing the catalyst. Certain other causes of catalyst deactivation that cannot be renewed by hydrogen treatment are often addressed by steam treatment and/or calcination in air, such treatments being carried out at high temperatures.

Regardless of the particular formulation, method of preparation, morphology and size of catalysts, all catalysts will undergo a loss in productivity and/or selectivity in use. Selectivity may vary with the particular synthesis, but is generally expressed in terms of the percent of an undesirable substance in the product mixture. For example, methane is an undesired presence in the Fischer-Tropsch product mixture since the object of the process is to form higher molecular weight hydrocarbons. Hence, one method of expressing the worth of a catalyst is its methane selectivity, i.e. the amount of undesirable methane in the reactor mixture.

Degradation of catalyst productivity may be due to a number of phenomena including contamination by catalytic poisons, deposition of carbonaceous residues, sintering, phase transformation of the metal or metals in the catalyst and the like. Attrition of the catalyst particulates may also occur and may lead to operational problems in slurry reactors due to the accumulation of fines, particles typically less than 10 microns in size. It is commercially significant to improve the operational reliability of the process and extend the useful life of a given catalyst prior to its disposal, for example, by means of regeneration.

In accordance with the present invention, significant enhancement in both the productivity and methane selectivity of catalysts for the Fischer-Tropsch synthesis is realized by treating a used catalyst to decrease the hydrocarbon content thereof; calcining in the presence of an oxidant-containing atmosphere, impregnating with an solution of at least one compound chosen from a group consisting of catalyst metals and promoter metals for the catalyst, again calcining in the presence of an oxidant-containing atmosphere and finally reducing with hydrogen-containing gas at elevated temperatures to form an active catalyst.

The term "used" catalyst in the context of the present invention means a catalyst that has been exposed to process conditions for the hydrogenation of carbon monoxide and, as a result, contains hydrocarbons. Used catalysts are first treated to decrease their hydrocarbon content, often referred to as "catalyst dewaxing". This may be carried out by one or more of several techniques. For example, separation may be effected by gravitational or centrifugal separation, which allows the hydrocarbon to be decanted, or removed by filtration, all of which require the hydrocarbons to be in a fluid state. The catalyst may also be treated with a solvent or supercritical fluid that effectively weakens the interaction of the hydrocarbons with the catalyst surface so that the liquid and solid phases can readily be separated in the same manner. This is referred to as solvent washing. Suitable solvents include, for example, paraffin solvents or naphthas, alcohols, and aromatic solvents. Supercritical fluids include, for example, carbon dioxide, light paraffins and cyclopentane.

Another means of decreasing the hydrocarbon content of used catalysts is to contact them with a hydrogen-containing gas at elevated temperatures, i.e. from about 200° C. to 600° C., preferably from 250° C. to 400° C. Typically, the hydrogen pressure would be from atmospheric to about 100 atm, preferably from atmospheric to 30 atm and gas hourly space velocities of from about 100 V/Hr/V to about 40,000 V/Hr/V, preferably from about 1,000 V/Hr/V to about 20,000 V/Hr/V, expressed as standard volumes of the hydrogen containing gas (25° C., 1 atm.) per hour per volume of catalyst, respectively. This treatment reduces at least a portion of the catalytic metal to its metallic state.

Alternatively, the catalyst may be contacted with an oxygen-containing gas or steam at elevated temperatures to effectively decrease the hydrocarbon content. Solvent washing, oxygen and hydrogen treatment may also be advantageously combined in the subject process. The duration of the dewaxing is adjusted to produce a low residual carbon content, for example less than 5 wt. %, preferably less than 2 wt. % and typically ranges from 30 minutes to about 8 hours. If the dewaxing step involves or includes contacting the catalyst with a solvent or supercritical fluid, it is preferably dried prior to the impregnation step described below. The dewaxing process may be carried out in any suitable reactor, including the HCS reactor itself For example, fixed bed HCS reactors are well suited for dewaxing by contacting the catalyst at elevated temperatures with reactive gases, such as hydrogen or an oxidant-containing gas. When using slurry bubble column HCS reactors it is preferred to withdraw a mixture of catalyst and hydrocarbons, more preferably during operation of the reactor and further treat the catalyst in a dedicated processing device.

Any of the foregoing techniques for dewaxing the catalyst are followed by contacting with an oxidant-containing gas at elevated temperatures to carry out the initial oxidation of the catalytic metal to its oxide. This step is often referred to as calcination. Typically, the calcination step in the process is to contact the catalyst with an oxidant-containing gas at elevated temperatures, i.e. from about room temperature to 600° C., preferably from room temperature to 400° C. The oxidant is chosen from the group consisting of air, oxygen, ozone and nitrogen oxides. When oxygen or air is used, the oxygen concentration in the gas may vary from 10 ppm to 21%. Preferably the temperature and the concentration of the oxidant in the oxidant-containing gas may be gradually increased to provide for control of the exotherm generated by the oxidation of the catalyst, particularly when the dewaxing was effected by hydrogen treatment at elevated temperatures. In the latter case, it may be advantageous to treat the catalyst with steam prior to calcination. Typically, the oxidant-containing gas pressure would be from atmospheric to about 100 atm, preferably from atmospheric to 30 atm and gas hourly space velocities of from about 100 V/Hr/V to about 40,000 V/Hr/V, preferably from about 1,000 V/Hr/V to about 20,000 V/Hr/V, expressed as standard volumes of gas (25° C., 1 atm.) per hour per volume of catalyst, respectively.

In accordance with the present invention, the calcined dewaxed catalyst is impregnated with a solution of at least one metal compound such as metal salts, metal complexes or metal-containing acids. The choice of solvent is dependent primarily on the capacity thereof to solubilize the metal compound. The solvent is preferably water, however, other solvents, e.g. certain organic solvents, may be combined therewith provided that they are miscible with water and do not introduce any known catalytic poison. Mixtures of water and immiscible organic solvents can be utilized as well as mixtures of water with solvents in combination with suitable dispersing or emulsifying agents present to form a continuous phase, i.e. an emulsion. Such other suitable liquids include hydrocarbons, particularly those derived from the Fischer-Tropsch synthesis, dense fluids, for example, supercritical fluids such as liquid phase light hydrocarbons, i.e. $C_{3-5}$, alkanes, cyclopentane and the like. Preferred mixed liquids include, without any intended limitation, water/lower alkanols, water/Fischer-Tropsch products, and water/alkanols/alkanes.

The metal compounds utilized in the treatment solution are preferably those that contain a catalytic metal or a promotor metal for the hydrogenation of carbon monoxide. Such catalytic metals include, but are not limited to Co, Ni, Cu, Ru, Pt, Rh, Ir, Os, Pd, whereas promotor metals include, but are not limited to Mo, W, Si, Cr, Ti, Mg, Mn, Zr, Hf Al, Th, La, Ce, Y and the like. The non-metal ions of the metal salts utilized in the impregnation solution are preferably those that are easily removable from the catalyst without the deposition of any material that might have a deleterious effect on the performance of the catalyst. Ions containing sulfur, halogens, phosphorus and the like are to be avoided. Preferred non-metal ions include, without intended limitation, nitrate, nitrite, cyanide and the like. The ion component of the metal salts may also be a weak organic acid moiety, such as carbonate, carboxylates and the like. Salts of those metals listed above that are amphoteric may be formed with ions such as ammonium and alkyl ammonium, wherein alkyl ammonium includes mono-, di-, tri- and tetra-alkyl ammonium ions or any mixture thereof Particularly preferred metal salts include the nitrate, acetate and, where applicable, the ammonium salt.

The carboxylate ions of the metal salts are defined as the salts derived from weak organic acids such as carboxylic acids having the general formula R—(COOH)$_n$ wherein n is 1–3 and R represents a cyclic or aliphatic, saturated or unsaturated moiety that may be substituted with one or more nitro, amino, hydroxyl or alkoxyl groups. Specific examples of suitable carboxylates include, without intended limitation, formates, acetates, citrate, succinate, malonate, propionate, butyrate, valerate, caproate, glutarate, adipate, lactate, benzoate, phthalate, salicylate, ascorbate, oxalate and the like. Preferred examples of suitable meta-containing acids include, without intended limitation, perrhenic acid, molybdic acids and tungstic acids. Metal complexes include, without intended limitation, metal acetylacetonate, metal ethylene diamine, metal diethylene triamines and the like.

The concentration of each of the constituents of the treatment solution will depend on a number of factors including the solubility of the complex, acid or salt, the volume of liquid utilized, the metal content and pore volume of the catalyst, the desired amount of metal to be added to the catalyst and the like. In general, the impregnating solution will contain from about 1 wt % to about 80 wt %, preferably from about 5 wt % to about 50 wt %, by weight of the metal compound. Typically, the amount of metal added to the catalyst will vary from about 1 wt % to about 80 wt % of the total metal content of the catalyst being impregnated, preferably 10 to 30 wt %. The solution of the metal compounds may be prepared by simply dissolving them in the selected solvent, or by combining solutions of suitable reactants.

The impregnation will typically be carried out until the catalyst substrate has absorbed a volume of impregnating solution equal to at least about 10% of its calculated pore volume, preferably to where conditions of incipient wetness are attained. By incipient wetness is meant that the substrate catalyst has adsorbed an amount of solution generally equivalent to its calculated pore volume. Pore volume is a discernible quantity that can be measured directly or indirectly by known techniques such as porosimetry. The volume of impregnating solution contemplated will vary from 10% to 5,000% of the calculated pore volume of the catalyst. Preferably, the volume of treatment solution will be from 30% to 1000%, most preferably from about 70% to 100% of the calculated pore volume of the catalyst.

The impregnating solution will remain in contact with the catalyst for from 1 minute to 24 hours, preferably from about 5 to 120 minutes. The time required for the treatment will vary depending on factors such as the quantity of the catalyst being treated, the composition and volume of the impregnating solution, the reactor configuration and the like. The treatment is carried out at a temperature from about 0° C. to about 100° C., preferably from room temperature, i.e. 20°–25° C., to about 80° C. The pressure is not particularly critical and can be from 0.1 to 100 atmospheres, with atmospheric pressure being preferred. The atmosphere is preferably air, but any non-reactive atmosphere is suitable. By non-reactive we mean an atmosphere that will not react with the solution during the impregnation step.

In the subject process, the catalyst impregnated as described above is then calcined under an oxidant-containing atmosphere prior to the activation step, preferably after drying the catalyst. The atmosphere is preferably air, but may be an inert atmosphere containing a controlled amount of oxygen, e.g. such as would be produced as a product gas stream or a waste gas stream from an air separation plant. Such controlled oxidant-containing atmospheres would contain from 10 ppm to 21% by volume, preferably from about 1% to 21% by volume, oxygen with the remainder being a non-oxidative gas, preferably an inert gas, such as nitrogen. The gas flow in the furnace is from about 100 to 10,000, preferably from about 1,000 to 5,000 GSHV. The calcination is carried out at elevated temperatures, i.e. from about 150° C. to about 600° C., preferably from about 200° C. to 450° C., for from about 1 to 8 hours, preferably from 1 to about 4 hours. Suitable apparatus for the calcining step may be a rotary calciner such as described in Perry's chemical Engineer's Handbook, Seventh Edition, Chapter 12, McGraw-Hill, N.Y.(1997), a fluidized processor as will be described below or an HCS reactor itself.

The treated catalyst particles are activated by reduction with hydrogen-containing gas at elevated temperatures, i.e. from about 200° C. to 600° C., preferably from about 250° C. to 400° C. Hydrogen partial pressure during the reduction would range from about 1 to 100 atmospheres, preferably from about 1 to 40 atmospheres, and the gas hourly space velocities would be from about 100 V/Hr/V to about 40,000 V/Hr/V, preferably from about 1,000 V/Hr/V to about 20,000 V/Hr/V, expressed as standard volumes of the gas or gas mixtures (25° C., 1 atm) per hour per volume of catalyst, respectively. The resulting catalyst particles regenerated in accordance with the present invention have been found to have a significant portion of their original activity restored, both in terms of production of the desired hydrocarbons and in methane selectivity.

It is a further optional step within the scope of the present invention to passivate the treated catalyst after the activation with hydrogen-containing gas has been carried out. The passivation may be carried out by contacting the catalyst with a gas containing carbon monoxide, or carbon monoxide and hydrogen, under conditions such that carbon monoxide does not significantly decompose and is not hydrogenated to a material degree. Such conditions, for example, would be a temperature below about 150° C., preferably between about 25° C. and 100° C., and pressure below about 20 atm, particularly between about 1 and 10 atm and the gas hourly space velocities would be from about 1 V/Hr/V to about 1,000 V/Hr/V, preferably from about 10 V/Hr/V to about 500 V/Hr/V, expressed as standard volumes of the gas or gas mixtures (25° C., 1 atm) per hour per volume of catalyst, respectively. It will be appreciated that some decomposition or hydrogenation, respectively, of the carbon monoxide may take place regardless of the precautions taken by the operator. However, it has been found that, typically, significant decomposition/hydrogenation will not take place wherein the concentration of carbon monoxide or carbon monoxide and hydrogen in the feed gas does not exceed about 5% by volume. Other passivating agents include, for example, traces of oxygen or carbon dioxide.

Often in commercial usage, a plurality of reactors is operated in parallel and in series. In accordance with the present invention, the treated catalyst is reused for the hydrogenation of carbon monoxide. The treatment may be effected in one or more reactors or in combination with other specialized apparatus as will be discussed below. All treating steps may be carried out in a single HCS reactor. Alternatively, the catalyst may be withdrawn and returned to at least one of said HCS reactors. It is within the scope of the present invention to carry out any up to all of the treating steps in the initial reactor prior to the withdrawing step, or in the subsequent one or more reactors after the returning step. Further, one or more of the treating steps may be carried out in the initial reactor or the subsequent one or more reactors and the remainder carried out in other specialized apparatus as will be described below. For example, when using a fixed bed HCS reactor, it is preferred to carry out at least the dewaxing step in the original reactor since it is well suited to such treatment.

When using slurry reactors, it is preferred to initially withdraw the catalyst as a mixture with hydrocarbon, typically molten wax, and carry out at least one of the treatment steps in specialized apparatus or the subsequent one or more reactors. While the amount of catalyst removed can vary within a wide range, those of ordinary skill in the art will appreciate that it is necessary that sufficient catalyst remain in the reactor to sustain the desired level of production. Generally, from about 0.01 wt. % to about 10 wt. % of the catalyst will be withdrawn from the reactor at a given point in time during production. It is not intended that such amount of catalyst be removed in a single quantity. Rather, portions of the withdrawn catalyst will be at various stages of the process of the invention at any given time so that, when a portion is returned to the subsequent one or more reactor, an estimated like amount can be withdrawn. It will be appreciated that, as utilized herein, the term "reactor" is not intended to be restricted to the singular and includes both the singular and the plural. When using the slurry reactor, it is a preferred option to continuously withdraw and replace catalyst while the reactor(s) is (are) in production.

The hydrocarbon content of the mixture withdrawn from the slurry reactor is essentially similar to that of the reactor at the mixture collection port. It is recognized that the hydrocarbon content of the mixture depends upon the type of reactor utilized, its configuration and operating conditions. For example, it is expected that a lower hydrocarbon content will be obtained when operating a bubble column reactor with a slumped bed as opposed to operating it with a dispersed bed. The mixture withdrawn from the reactor may be initially treated by conventional techniques, for example by physical screening, to separate the fines from the remaining catalyst particles. Although the criteria for what are classified as fines particles may vary with the reactor, generally fines are recognized as particles smaller than 10 microns.

Formation and accumulation of fines through attrition of the catalyst particles can result from normal operation of the reactor or from processing of the withdrawn catalyst. Accumulation of fines in the reactor can lead to operational problems. Many methods are recognized as useful for removing fines. For example, fines may be removed by classifying or screening of dry flowing powders or decantation of catalyst slurry after a specified catalyst settling time. Even though the removal of fines may be effected on dry catalyst or catalyst slurry obtained prior to returning the catalyst to a reactor, it is preferred to remove the fines during or after the dewaxing step. The activity of the supported catalyst particles separated from the fines will be enhanced in accordance with the subject invention. The fines, which may be composed of both catalyst and support material, may be processed into, for example, useful catalyst or further processed for metal recovery.

As stated above, the treatment process in accordance with the present invention may be carried out in one or more HCS reactors, in a series of apparatus particularly adapted to a specific step or steps or any combination thereof. For example, the step of decreasing the hydrocarbon content of a catalyst withdrawn from an HCS slurry reactor may advantageously be carried out in a mixer-settler vessel as is described in Perry's Chemical Engineers' Handbook, Seventh Edition, Chapter 18, McGraw-Hill, N.Y. 1997. Such a vessel would typically be provided with a heating jacket, agitator and liquid phase withdrawing means. After treatment therein, the catalyst would be withdrawn, typically as a slurry, and be passed to a processor for solvent removal and drying.

The processor is a device that can impart mixing and fluidization to the process. It would be configured to enhance heat transfer, mixing liquid-contacting, and gas solid transfer. Examples of suitable processors are gas fluidized beds, vibro-fluidized beds, mechanical blenders, e.g. double cone, vee, ribbon and the like and mixers such as plow, planetary, paddle and the like. These devices fluidize the processed material by passing a gas directly through it, by mechanical agitation or by a combination of both actions. Processing in such a device causes the material being treated to attain fluid-like properties resulting in intimate contact between each particle and the gas stream thus creating an extremely efficient mass and heat transfer. A devices that provides at least mechanical fluidization is particularly preferred since, although both a slurry and a powder can be made to readily flow, during the drying process from one to the other, the material will pass through what is termed the "mud stage" where it is extremely difficult to fluidize. Hence, for the drying operation wherein a catalyst is in a slurry, the processor should have at least mechanical and, preferably, both mechanical and gas fluidization.

A preferred processor for carrying out the subject process is the plow mixer, a device with a jacketed horizontal cylinder with an axial agitator shaft containing several sets of blade or triangular agitators. Such a device will typically also have both gas and liquid inlets and outlets as well as an inlet and outlet for the solid material being processed. While this is a preferred device, any comparable mixer possessing the foregoing capabilities could be utilized as well, provided that it has the capacity to continue to fluidize the material through the mud stage of drying. Such a device will also facilitate the solvent washing that can be part of the process of decreasing the hydrocarbon content of the material as well as the subsequent hydrogen treatment at elevated temperatures. This is a preferred method of decreasing hydrocarbon content since it permits recovery of the wax, an important consideration.

The next step, calcining of the dried catalyst may be carried out in the processor, or is a suitable device as described above. Following calcination, the treatment with the impregnation solution as described above can likewise be carried out in a mechanical mixer, such as a plow mixer for the reasons previously stated. The mixer is advantageous in that the liquid may be added while the material is in a fluidized condition. Because the mixer has inlet and outlet means for gas, when the material has been impregnated to the desired degree, the subsequent calcination in an oxidant-containing atmosphere may be affected therein as well. The material may remain in the processor, or may be removed for further processing, for example, the removal of fines, drying and calcination steps discussed above. All of these operations may be carried out in the processor if desired. However, suitable devices for removal of fines from dry particulate solids, for example by sieving, elutriation from fluidized beds, gas classification and the like, are described in Perry's Chemical Engineers' Handbook, Seventh Edition, Chapters 17, 19 and 20, McGraw-Hill, N.Y. 1997.

The final activation of the material to form an active catalyst can be carried out in a fluidized processor as described above. A larger variety of devices may be utilized for this step, however, since the material does not pass through a mud phase, hence gas fluidizers can be utilized for the excellent solidlo gas contact they provide. It is particularly useful when the catalyst has undergone the decrease of hydrocarbon content in a fixed bed reactor. Further, a gas fluidizer may be utilized for the activating the catalyst, reducing a fresh batch of catalyst and optionally for the passivation step described above as, again, the material does not transcend through a mud phase. It can be appreciated, that a series of varied devices can be utilized to carry out the process of the present invention, which may be advantageous for large-scale operations. However, as described above, it is also possible to carry out the entire process of regeneration of the used catalyst in a mechanical fluidizer having the capabilities of solid, gas and liquid transfer.

It is understood that various other embodiments and modifications in the practice of the invention will be apparent to, and can be readily made by, those of ordinary skill in the art without departing form the scope and spirit of the invention as described above. Accordingly, it is not intended that the scope of the claims appended hereto be limited to the exact description set forth above, but rather that the claims be construed as encompassing all of the features of patentable novelty that reside in the present invention, including all the features and embodiments that would be treated as equivalents thereof by those skilled in the art to which the invention pertains. The invention is further described with reference to the following experimental work.

EXAMPLE 1
Solvent Dewaxed Catalyst

Chunks of cobalt-based catalyst on a titania support in wax that were removed from a Fischer-Tropsch reactor in operation for over two hundred days weighing 83 grams were placed in a beaker and covered with toluene. The mixture was heated to 85–90° C. and stirred by hand. The chunks broke apart during the heating/stirring. After 5 minutes, the toluene/wax solution was decanted, fresh toluene added and the process repeated twice more. After the third decanting, the remaining toluene/catalyst slurry was transferred to a Buchner funnel and filtered hot. Hot toluene was poured onto the filter cake three times and drawn through the filter cake by applied vacuum. The filter cake was dried on the funnel by the application of vacuum to yield 58.4 grams of non-pyrophoric catalyst. The catalyst contained substantial amounts of reduced cobalt as indicated by its high magnetic permeability. The catalyst was easily moved with a small permanent magnet. A second sample was prepared in a like manner with the additional step of being air dried overnight after being dried on the funnel. Its characteristics were the same.

EXAMPLE 2
Testing of Catalyst from Example 1

The catalyst from Example 1 was tested in a laboratory fixed bed reactor. The catalyst (2 mL, 2.80 g) was mixed with a quartz diluent (4 mL, 6.54 g) and placed into a 1 cm inside diameter tubular reactor. The catalyst bed was held in place with a plug of glass wool. A multi-point thermocouple was inserted into the bed to monitor temperatures. The catalyst was initially reduced by hydrogen at 375° C., 19.7 atm and 315 sccm of hydrogen over two hours. The catalyst was cooled to 177° C., 19.7 atm under a flow of 10 sccm argon and 260 sccm hydrogen. After cooling, the feed composition was changed 12 sccm argon, 134 sccm hydrogen and 94 sccm of a carbon monoxide/carbon dioxide blend, giving a nominal feed composition of 56.0% $H_2$, 11.6% $CO_2$, 4.9% Ar and 27.5% CO, wherein the percentages are given as mole percents. The reactor was then heated at 2.8° C./hour to 199° C. and held at temperature for 24 hours. The reactor was then heated at 2.8° C./hour to 213° C. and held at temperature for the remainder of the test. At this temperature, the CO conversion was 27.3% and the methane selectivity was 7.6%. After 24 hours under these conditions, the CO conversion was 24.3% and the methane selectivity was 7.6%. Methane selectivity is defined as the carbon in the methane produced as a fraction of the carbon in the converted carbon monoxide.

EXAMPLE 3
Air Regeneration of Solvent Dewaxed Catalyst

Thirty grams of catalyst from Example 1 were placed in a ceramic dish and calcined in air at 300° C. for two hours. The calcined catalyst was recovered as a dry dark gray powder. The calcined catalyst was tested for catalytic activity according the procedure described in Example 4. The CO conversion was 55.0% and the methane selectivity was 10.9%. After 24 hours under these conditions, the CO conversion was 52.4% and the methane selectivity was 10.5%. This example demonstrates that catalytic activity can be recovered by air calcination of the deactivated catalyst

EXAMPLE 4
Cobalt Nitrate Addition to Air Regenerated Catalyst

A solution was prepared by adding 37.03 grams of cobalt nitrate hexahydrate to approximately 25 ml of deionized water under a nitrogen atmosphere and diluting to a total volume of 50 ml. The solution was heated gently to dissolve all solids completely and stored under the nitrogen atmosphere. A total of 2.60 grams of the cobalt nitrate solution was added to ten grams of the dewaxed catalyst form example 3 that had been calcined at 300° C. for 2 hrs. No exotherm occurred and no color change was observed. After an additional 2 hours in air, the sample was dried at 100° C. for 1 hr and then calcined at 300° C. for 2 hours. 11.2 Grams of a dark gray powder were recovered.

The calcined catalyst was tested for catalytic activity according the procedure described in example 2. After reaching 213° C., the CO conversion was 65% and the $CH_4$ selectivity was 7.8%. After 1 day at this condition, the CO conversion was 63% and the $CH_4$ selectivity was 7.5%. This example shows that catalytic activity and selectivity of an air regenerated catalyst can further be enhanced by addition of catalytic metal.

What is claimed is:

1. A process for the enhancement of a used metal catalyst for the catalytic hydrogenation of carbon monoxide, said catalyst comprising one or more members selected from the group consisting of Co, Ni, Cu, Ru, Rh, Pd, Os, Ir, Re and Pt, the process comprising:
   a) decreasing the hydrocarbon content thereof;
   b) calcining under an oxidant-containing atmosphere;
   c) impregnating with a solution of a compound of at least one metal selected from the group consisting of Co, Ni, Cu, Ru, Rh, Pd, Os, Ir, Re, Pt, Mo, W, SI, Cr, Ti, Mg, Mn, Zr, Hf, Al, Th, and Y;
   d) calcining under an oxidant-containing atmosphere; and
   e) reducing with a hydrogen-containing gas at elevated temperatures thereby forming an active catalyst.

2. A process in accordance with claim 1, wherein step a) is carried out by one of the following:
   contacting with a hydrogen-containing gas at elevated temperatures;
   treating with a solvent or supercritical fluid;
   treating with a solvent or supercritical fluid and then contacting with a hydrogen-containing gas at elevated temperatures;
   contacting with an oxygen-containing gas or steam at elevated temperatures and then contacting with a hydrogen-containing gas at elevated temperatures; and
   treating with a solvent or supercritical fluid, contacting with an oxygen-containing gas or steam at elevated temperatures and then contacting with a hydrogen-containing gas at elevated temperatures.

3. A process in accordance with claim 1, wherein the impregnation solution in step c) contains a compound of a metal selected from the group consisting of cobalt, ruthenium, copper and nickel.

4. A process in accordance with claim 1, wherein the metal compound in step C) is a metal salt selected from the group consisting of nitrate, acetate, formate, citrate and carbonate.

5. A process in accordance with claim 1, wherein the impregnation solution in step C) contains a salt of the same metal as the catalyst metal.

6. A process in accordance with claim 1 wherein said oxidant in step b) or d) is selected from the group consisting of oxygen, air, ozone and nitrogen oxides.

7. A process in accordance with claim 1 wherein the amount of said impregnating solution utilized in step c) is from about 10% to 5,000% of the calculated pore volume of the catalyst.

8. A process in accordance with claim 1 additionally including the step of passivating after step e) by:
   treatment with a carbon monoxide-containing gas under conditions such that the carbon monoxide is not significantly decomposed; or
   treatment with a gas containing carbon monoxide and hydrogen under conditions such that the carbon monoxide is not significantly hydrogenated.

9. A process in accordance with claim 1, wherein said catalyst comprises cobalt.

10. A catalyst for the hydrogenation of carbon monoxide, comprising one or more members selected from the group consisting of Co, Ni, Cu, Ru, Rh, Pd, Os, Ir, Re and Pt, said catalyst being enhanced by the process of claim 1.

11. A process for producing higher hydrocarbons by the hydrogenation of carbon monoxide by reaction with hydrogen at reaction conditions in the presence of an enhanced catalyst according to claim 10.

12. A process in accordance with claim 11, wherein at least a portion of the hydrocarbons formed are upgraded to more valuable products by at least one of fractionation and conversion operations.

13. A process for the catalytic hydrogenation of carbon monoxide to produce a mixture of hydrocarbons in a carbon monoxide hydrogenation reactor utilizing a used catalyst comprising one or more members selected from the group consisting of Co, Ni, Cu, Ru, Rh, Pd, Os, Ir, Re and Pt, at least a portion of the catalyst having been enhanced by a process comprising:
   a) decreasing the hydrocarbon content thereof;
   b) calcining under an oxidant-containing atmosphere;
   c) impregnating with a solution of a compound of at least one metal selected from the group consisting of Co, Ni, Cu, Ru, Rh, Pd, Os, Ir, Re, Pt, Mo, W, SI, Cr, Ti, Mg, Mn, Zr, Hf, Al, Th, and Y;
   d) calcining under an oxidant-containing atmosphere; and
   e) reducing with a hydrogen-containing gas at elevated temperatures thereby forming an active catalyst.

14. A process in accordance with claim 13, additionally including the step of removing catalyst fines by
   i) classification or screening of a powder obtained in any step producing a powder; or
   ii) decanting or classification of a catalyst slurry in any step producing a slurry.

15. A process in accordance with claim 13, wherein said catalyst is a supported catalyst.

16. A process in accordance with claim 13, wherein said catalyst is a Dispersed Active Metal (DAM) catalyst.

17. A process in accordance with claim 13, wherein said catalyst comprises cobalt.

18. A process according to claim 13, wherein steps (a through (e are carried out in a single carbon monoxide hydrogenation reactor.

19. A process according to claim 18, wherein the carbon monoxide hydrogenation reactor is a fixed bed reactor.

20. A process according to claim 13, additionally including the steps of withdrawing catalyst from a reactor and returning it to at least one reactor, wherein steps (a through (e are carried out subsequent to said withdrawing step.

21. A process according to claim 20, where steps (a through (e are carried out prior to said returning step.

22. A process according to claim 20, where steps (a through (e are carried out subsequent to said returning step.

23. A process according to claim 20, wherein said reactors are slurry reactors and the catalyst is withdrawn as a mixture with hydrocarbons.

24. A process in accordance with claim 23, wherein in step a) the catalyst particles are initially separated from the mixture.

25. A process in accordance with claim 24, wherein the catalyst particles are separated by filtration, or by gravitational or centrifugal separation followed by decanting the hydrocarbons from the catalyst particles.

26. A process in accordance with claim 23, wherein the treated catalyst is returned in at least one slurry reactor by one or more of:
   forming a slurry of the catalyst with liquid hydrocarbons and introducing said slurry into said reactor;
   forming a suspension of the catalyst in a non-oxidizing gas and introducing said suspension into said reactor, or
   transferring the catalyst to the reactor by gravity or pressure gradient.

27. A process in accordance with claim 23, wherein said catalyst is withdrawn periodically during operation of at least one slurry reactor.

28. A process according to claim 23, wherein at least a portion of said catalyst is returned to at least one slurry reactor during operation thereof.

29. A process in accordance with claim 23, wherein said catalyst is withdrawn continuously during operation of at least one slurry reactor.

30. A process according to claim 13, additionally including the steps of withdrawing catalyst from a reactor and returning it to at least one reactor, wherein at least one of steps (a through (e is carried out prior to said withdrawing step.

31. A process according to claim 30, wherein at least one of steps (b through (e is carried out prior to said returning step.

32. A process according to claim 13, additionally including the steps of withdrawing catalyst from a reactor and returning it to at least one reactor, wherein at least one of steps (a through (d is carried out prior to said withdrawing step, and at least one of steps (b through (a is carried out subsequent to said returning step.

33. A process according to claim 32, wherein the catalyst is passivated after step a) and then withdrawn from the reactor.

* * * * *